United States Patent [19]
Knuteson

[11] Patent Number: 6,134,477
[45] Date of Patent: Oct. 17, 2000

[54] ADJUSTABLE MEDICAL LEAD FIXATION SYSTEM

[75] Inventor: Eric A. Knuteson, Stillwater, Minn.

[73] Assignee: Medtronic, Inc., Minneapolis, Minn.

[21] Appl. No.: 09/302,615

[22] Filed: Apr. 30, 1999

[51] Int. Cl.⁷ .................................................. A61N 1/02
[52] U.S. Cl. ................................................................. 607/115
[58] Field of Search ................................... 607/115, 139; 608/373, 377, 378, 383, 386; 604/174, 178; 128/899

[56] References Cited

U.S. PATENT DOCUMENTS

| | | |
|---|---|---|
| 3,115,140 | 12/1963 | Volkman . |
| 4,328,813 | 5/1982 | Ray .......................................... 128/791 |
| 5,026,352 | 6/1991 | Anderson ................................. 604/178 |

*Primary Examiner*—William E. Kamm
*Attorney, Agent, or Firm*—Banner & Witcoff, Ltd.

[57] ABSTRACT

There is disclosed an adjustable medical apparatus for anchoring a lead to a cranial burr hole. The apparatus comprises generally an anchoring plate mounted to and over a cranial burr hole, an anchoring arm pivotally mounted to the anchoring plate, and a resilient sleeve mounted between the anchoring plate and the anchoring arm. The resilient sleeves defines an aperture for receiving the lead. Once an implanted lead is inserted into the aperture in the resilient sleeve, the anchoring arm is pivoted around the sleeve creating a clamping force on the resilient sleeve. The resilient sleeve in turn creates a clamping force on the lead body, thereby anchoring the lead relative to the anchoring apparatus and thus relative to the cranium. Significantly, the anchoring apparatus accommodates various sized lead bodies which are used within various sized burr holes.

17 Claims, 1 Drawing Sheet

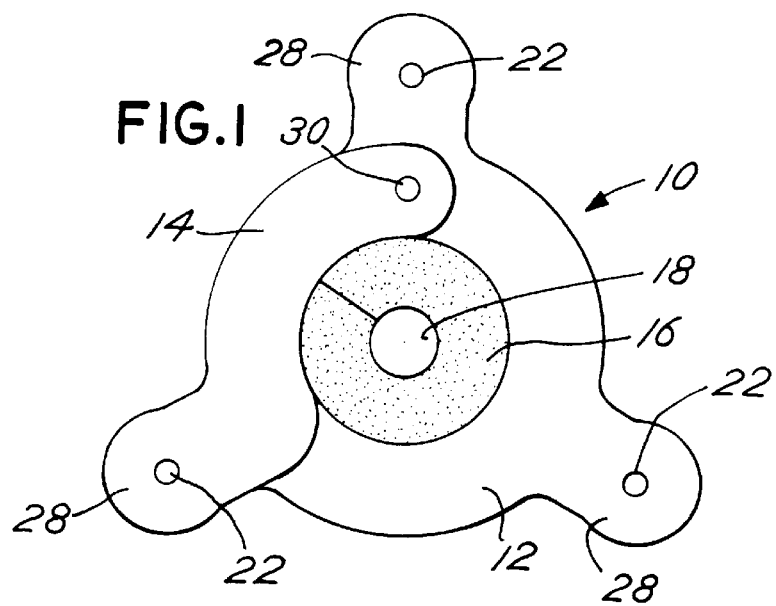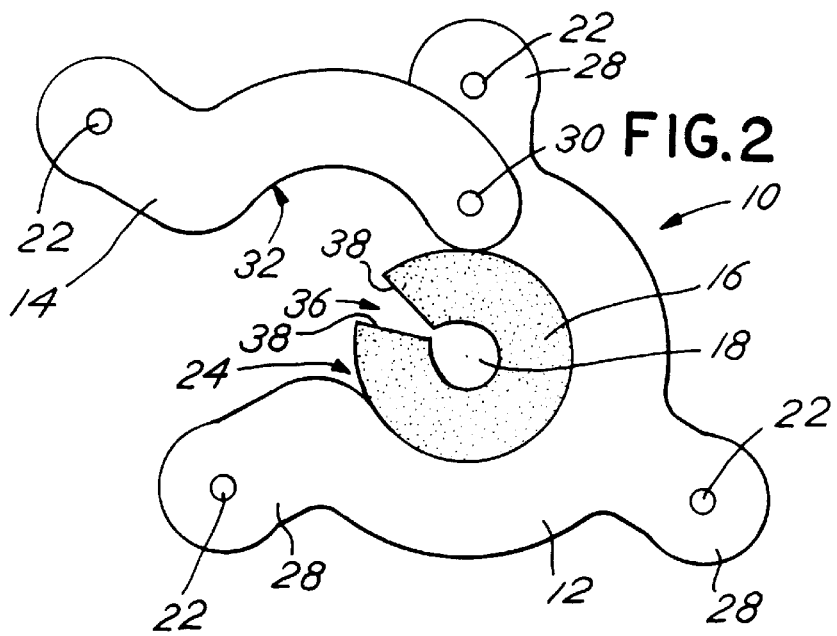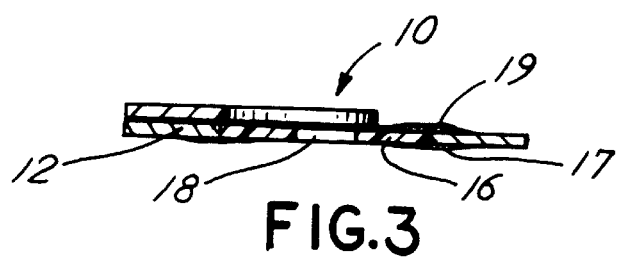

ADJUSTABLE MEDICAL LEAD FIXATION SYSTEM

BACKGROUND OF THE INVENTION

1. Field of the Invention

The present invention relates to an apparatus for securing implanted medical devices and more particularly to an apparatus for securing implanted medical devices such as electrical stimulation leads to various sized cranial burr holes.

2. Description of the Related Art

Medical procedures involving access to the brain through a burr hole in the skull are under increasing use. One such procedure is electrical stimulation of the brain for such purposes as relief of chronic pain and treatment of movement disorders. A typical electrical brain stimulation system comprises generally a pulse generator operatively connected to the brain by a lead having at its distal end at least one electrode designed to be implanted within the brain, and having at its proximal end a connector assembly designed to connect to the pulse generator.

An important aspect of this procedure, and of any other such procedures that involve instrument access to the brain through a burr hole, is the precision with which any such inserted stimulation devices are placed. As can be appreciated, the functional location of the inserted stimulation device is of critical importance and once an inserted device is properly positioned, it is equally important that the device not be moved. Even one millimeter of travel of a properly positioned stimulation device may cause unsatisfactory results. Accordingly, reliable methods and apparatus for stabilizing and fixing the positioned stimulation device in the cranial burr hole are necessary.

Previous designs of systems for securing a positioned device within a burr hole have a number of drawbacks. U.S. Pat. No. 4,328,813 issued to Ray, incorporated herein by reference, discloses a burr hole ring and cap arrangement in which the cap is positioned so as to trap a positioned electrical stimulation lead between the ring and cap by friction. The ring and cap arrangement in Ray, however, is limited by the size of the lead bodies which can be used within a single burr hole ring. Other known burr hole ring and cap assemblies have the same drawbacks. A single burr hole ring can only accommodate a limited size or range of sizes of the lead bodies. The present invention is directed to overcoming these disadvantages of the present burr hole ring and cap anchoring assemblies. Banner & Witcoff, Ltd.

SUMMARY OF THE INVENTION

As explained in more detail below, the present invention overcomes the above-noted and other shortcomings of prior burr hole anchoring devices.

The present invention preferably comprises an apparatus fixing a lead at a cranial burr hole. An important feature of the invention is that the disclosed anchoring apparatus may be used with various sized lead bodies which may be implanted in various sized burr holes. A second important aspect of the invention is that the disclosed device can be used with various sized burr holes. Thus, one anchoring device of the present invention will accommodate numerous lead bodies and burr holes of differing diameters.

Briefly, the present invention generally comprises an anchoring plate, a pivotable anchoring arm, and a resilient inner sleeve. The resilient inner sleeve defines a slit which extends along the longitudinal length of sleeve and an aperture for receiving various sized lead bodies. As assembled, the anchoring plate is fastened to the cranium. Pivotally attached to the anchoring plate is the anchoring arm. The anchoring plate and anchoring arm define an opening to receive the resilient inner sleeve. In use, a lead is inserted through the aperture of the resilient inner sleeve into the cranial burr hole. Once the lead is located along the proper track to the desired depth and location in the brain, the inner sleeve is positioned within the opening formed in the anchoring plate. The anchoring arm is then closed around the inner sleeve creating a uniform clamping force on the inner sleeve. The inner sleeve defining a longitudinal slit, in turn, permits the inner sleeve to close around the lead body, creating a uniform clamping force on the lead body, thereby anchoring the lead relative to the cranium. Significantly, the opening formed by the anchoring plate and arm, and the design of the inner sleeve, accommodate numerous lead bodies of varying diameters. Moreover, the present invention can be used with smaller leads in larger burr holes where the lead may be positioned off-center in the burr hole.

Examples of the more important features of this invention have been broadly outlined above in order that the detailed description that follows may be better understood and so that contributions which this invention provides to the art may be better appreciated. There are, of course, additional features of the invention which will be described herein and which will be included within the subject matter of the claims appended hereto.

BRIEF DESCRIPTION OF THE DRAWINGS

The preferred embodiments of the invention will be described in relation to the accompanying drawings. In the drawings, the following figures have the following general nature:

FIG. 1 is a top plan view of the adjustable lead anchoring device of the present invention.

FIG. 2 is another top plan view of the invention of FIG. 1.

FIG. 3 is a side view of the invention of FIG. 1.

In the accompanying drawings, like reference numbers are used throughout the various figures for identical structures.

DESCRIPTION OF THE PREFERRED EMBODIMENTS

Referring to FIGS. 1–3, a preferred adjustable medical lead anchoring system is depicted. The preferred anchoring system 10 comprises generally an anchoring plate 12, an anchoring arm 14 and a resilient inner sleeve 16. The resilient inner sleeve defines an aperture 18 for receiving medical leads of varying diameters. As used herein, the term "lead" may refer to any elongated medical apparatus having an electrode providing electrical stimulation, or a parenchymal catheter for infusing pharmaceutical agents. The selection of one lead over another will depend on numerous factors such as the therapy being delivered. The selection of the burr hole size will depend on numerous factors including surgical preference. As most preferred, the aperture 18 accommodates lead bodies which fit within burr holes having varying diameters of up to 14 millimeters.

The anchoring plate 12 is preferably a rigid flat plate anchored to the cranium through the use of mounting screws, not shown. As conventional, three mounting screws are used to stabilize and fix the plate 12 to the cranium. The anchoring plate 12 defines a plurality of mounting holes 22 for receiving the mounting screws. The plate 12 also defines a semi-circular opening 24 sized and shaped to receive the inner sleeve 16. That is, the opening 24 has a diameter slightly larger than the outer diameter of the sleeve 16 in its unsprung state. As depicted in plan view, the plate 12 has a preferable semi-circular shaped body with three anchoring legs 28 radially protruding outward from the semi-circular body. Located within each of the three anchoring legs are the mounting holes 22. As one can imagine, other similar means for anchoring the plate to the cranium may be used and are considered within the scope of the present invention.

Pivotally mounted to the anchoring plate 12 is the anchoring arm 14. The anchoring arm 14 is pivotally mounted to the anchoring plate 12 by means of a pivot pin 30. The anchoring arm 14 is also a rigid flat plate. In plan view, the anchoring arm 14 is arcuate in shape and defines a mounting hole 22. The arcuate shaped anchoring arm forms a curve or radius 32 which is sized and shaped to match the contour of the inner sleeve 16. The anchoring plate and arm may be made of stainless steel, rigid plastic, or any other suitable rigid material.

In use, once the inner sleeve 16 is positioned within the opening 24, the anchoring arm 14 is pivoted around the inner sleeve with the curve 32 contacting the inner sleeve 16. As the anchoring arm is further pivoted around the inner sleeve 16, the anchoring arm 14 and the anchoring plate 12 exert a clamping force on the exterior of the inner sleeve. As discussed in further detail below, the inner sleeve, which envelops the lead body, in turn, exerts a clamping force on the lead body, thereby stabilizing and fixing the lead relative to the anchoring plate and the cranium. Advantageously, prior to anchoring the plate 12 to the cranium, the lead may be positioned anywhere within the larger sized burr holes, to accommodate off-center lead tracks. The free end of the anchoring arm, opposite the pivot end, is then fixed or fastened to the anchoring plate or directly to the cranium, thereby holding the inner sleeve in the clamped position.

The resilient inner sleeve 16 is positioned above the cranial burr hole and within the opening 24 of the anchoring plate 12. The inner sleeve further defines a cylindrical body having a slit 36 extending along the longitudinal length of the body. The slit 36 permits the radial expansion and contraction of the sleeve 16 to accommodate the various sized lead bodies. The cylindrical ends 38 of the sleeve 16 are angled to permit the sleeve to snap around the lead body. The inner sleeve 16 further defines the aperture 18 for receiving lead bodies of various diameters. As preferred, the sleeve 16 defines an unsprung outer diameter sized to fit within the opening 24. The inner sleeve may be made of rubber or other similar elastomeric material. As depicted in FIG. 3, the inner sleeve 16 may form around the top and bottom of the plate 12. That is, inner sleeve material may protrude radially outward on the bottom of the plate 12. This additional material, identified by item 17, serves as a seal to prevent leakage of cerebrospinal fluid (CSF). In addition, inner sleeve material may protrude radially outward on the top of the plate 12. This material, identified by item 19, forms a crown or radius to permit the lead to be bent over the plate 12. Radial grooves may be formed in this additional material to guide the lead in a radial direction away from the burr hole. Other shapes and designs of the inner sleeve which permit clamping around the lead body are contemplated and are considered within the spirit and scope of the present invention.

Once the lead is properly located and positioned within the cranial burr hole, the anchoring system 10 may be positioned around the lead anchoring the lead to the cranium. The method for anchoring the lead includes the following steps. First, the sleeve is pretooled or positioned within the opening 24 in the anchoring plate 12. Next, the anchoring system 10 is placed around the lead body, with the lead passing through the opening 24 in the sleeve, and lowered to the cranium. Then the anchoring arm 14 is pivoted around the sleeve closing the sleeve around the lead body. The anchoring device is then anchored, through the use of anchoring screws, to the cranium over the burr hole. Advantageously, the closure of the sleeve around the lead creates a clamping force on the lead body fixing the lead in the desired position.

The preferred embodiments of the invention are now described as to enable a person of ordinary skill in the art to make and use the same. Variations of the preferred embodiment are possible without being outside the scope of the present invention. Therefore, to particularly point out and distinctly claim the subject matter regarded as the invention, the following claims conclude the specification.

What is claimed is:

1. An adjustable medical apparatus for fixing a lead in a cranium burr hole comprising:
   an anchoring plate mounted over the cranium burr hole,
   an anchoring arm pivotally mounted to the anchoring plate, and
   an inner sleeve mounted to the anchoring plate.

2. The adjustable medical apparatus of claim 1 wherein the anchoring plate and anchoring arm define an opening for receiving the inner sleeve.

3. The adjustable medical apparatus of claim 1 wherein the inner sleeve is resilient.

4. The adjustable medical apparatus of claim 1 wherein the inner sleeve defines an aperture for receiving the lead.

5. The adjustable medical apparatus of claim 1 wherein the inner sleeve defines a cylindrical body having a slit extending along the longitudinal length of the cylindrical body.

6. The adjustable medical apparatus of claim 1 wherein the anchoring plate defines a plurality of attachment holes for mounting the anchoring plate to the cranium.

7. An adjustable medical apparatus for fixing a lead in a cranium burr hole comprising:
   an anchoring plate mounted over the cranium burr hole,
   an anchoring arm pivotally mounted to the anchoring plate, the anchoring arm and anchoring plate defining an opening, and
   a resilient inner sleeve mounted in the opening defined by the anchoring arm and plate.

8. The adjustable medical apparatus of claim 7 wherein the inner sleeve defines an aperture for receiving the lead.

9. The adjustable medical apparatus of claim 7 wherein the inner sleeve defines a cylindrical body having a slit extending along the longitudinal length of the cylindrical body.

10. The adjustable medical apparatus of claim 7 wherein the anchoring plate defines a plurality of attachment holes for mounting the anchoring plate to the cranium.

11. An adjustable medical apparatus for fixing a lead in a cranium burr hole comprising:
    an anchoring plate mounted over the cranium burr hole,
    an anchoring arm pivotally mounted to the anchoring plate, the anchoring arm and anchoring plate defining an opening, and
    a resilient inner sleeve mounted in the opening defined by the anchoring arm and plate, the resilient inner sleeve defining a cylindrical body having a slit extending along the longitudinal length of the cylindrical body.

12. The adjustable medical apparatus of claim 11 wherein the anchoring plate defines a plurality of attachment holes for mounting the anchoring plate to the cranium.

13. The adjustable medical apparatus of claim 11 wherein the inner sleeve defines an aperture for receiving the lead.

14. A method for anchoring a medical lead in a cranial burr hole, comprising the steps of:

providing an anchoring plate, providing an anchoring arm pivotally mounted to the anchoring plate, the anchoring arm and anchoring plate defining an opening, mounting a resilient inner sleeve in the opening defined by the anchoring arm and anchoring plate, positioning the lead within the cranial burr hole, positioning the anchoring plate over the cranium burr hole and around the lead, positioning the lead within the resilient inner sleeve, rotating the anchoring arm around the resilient inner sleeve, and fixing the anchoring plate to the cranium.

15. The method of claim 14 wherein the inner sleeve defines an aperture for receiving the lead.

16. The method of claim 14 wherein the anchoring plate defines a plurality of attachment holes for mounting the anchoring plate to the cranium.

17. The method of claim 14 wherein the inner sleeve defines a cylindrical body having a slit extending along the longitudinal length of the cylindrical body.

* * * * *

UNITED STATES PATENT AND TRADEMARK OFFICE
CERTIFICATE OF CORRECTION

PATENT NO. : 6,134,477
DATED : October 17, 2000
INVENTOR(S) : Eric A. Knuteson

It is certified that error appears in the above-identified patent and that said Letters Patent is hereby corrected as shown below:

Col. 1, ln. 48: remove "Banner & Witcoff, Ltd."

Signed and Sealed this

Eighth Day of May, 2001

*Attest:*

NICHOLAS P. GODICI

*Attesting Officer*     Acting Director of the United States Patent and Trademark Office